United States Patent [19]
Stavely et al.

[11] Patent Number: 5,969,372
[45] Date of Patent: Oct. 19, 1999

[54] FILM SCANNER WITH DUST AND SCRATCH CORRECTION BY USE OF DARK-FIELD ILLUMINATION

[75] Inventors: Donald J. Stavely, Windsor; Daniel M. Bloom, Loveland; Amy E. Battles, Greeley; David K. Campbell, Loveland; Oscar R. Herrera E., Greeley, all of Colo.

[73] Assignee: Hewlett-Packard Company, Palo Alto, Calif.

[21] Appl. No.: 08/949,507

[22] Filed: Oct. 14, 1997

[51] Int. Cl.⁶ .................................................. G01N 21/88
[52] U.S. Cl. .................................... 250/559.42; 356/239
[58] Field of Search ............................ 250/234–236, 250/208.1, 559.48, 559.49, 559.02; 356/237–239

[56] References Cited

U.S. PATENT DOCUMENTS

| 4,232,937 | 11/1980 | Swaminathan et al. | 350/91 |
|---|---|---|---|
| 4,265,545 | 5/1981 | Slaker | 250/559.49 |
| 4,734,578 | 3/1988 | Horikawa | 250/234 |
| 4,972,091 | 11/1990 | Cielo et al. | 250/559.42 |
| 5,179,422 | 1/1993 | Peterson | 250/559.41 |
| 5,266,805 | 11/1993 | Edgar | 250/330 |
| 5,665,963 | 9/1997 | Campbell | 250/226 |

FOREIGN PATENT DOCUMENTS

WO98/31142 7/1998 WIPO.
WO98/34397 8/1998 WIPO.

OTHER PUBLICATIONS

"Automated Digital Visual Inspection With Dark–Field Microscopy", by Jorge L.C. Sanz, Fritz Merkle and Kwan Y. Wong. 1985 Optical Society Of America, Nov. 1985, vol. 2, No. 11.

"Designing A Scanner With Color Vision", by K. Douglas Gennetten and Michael J. Steinle. Aug. 1993 Hewlett–Packard Journal.

*Primary Examiner*—Stephone Allen

[57] ABSTRACT

A method and apparatus for detecting surface defects and artifacts on a transmissive image in an optical image scanner and correcting the resulting scanned image. In one scan, the image is scanned normally. Surface defects and artifacts such as dust, scratches and finger prints are detected by providing a separate scan using infrared light or by measuring light (white or infrared) that is scattered or diffracted by the defects and artifacts. Separate optical paths for illumination may be used, or separate optical paths for intensity measurement may be used. Image processing may then be used to correct areas in the normal scan corresponding to defects identified in the separate scan.

16 Claims, 10 Drawing Sheets

FILM SCANNER WITH DUST AND SCRATCH CORRECTION BY USE OF DARK-FIELD ILLUMINATION

FIELD OF INVENTION

This invention relates generally to devices for digital electronic scanning of images and more specifically to correction for dust and scratches when scanning transmissive images.

BACKGROUND OF THE INVENTION

Electronic image scanners convert an optical image into an electronic form suitable for storage, transmission or printing. Film scanners are used, for example, for X-ray films, developed negative film strips, and slide film (also called reversal film or "chrome" film). In a typical image scanner, light from an image is focused onto linear arrays of photosensors for scanning one line at a time. A two dimensional image is scanned by providing relative movement between the linear sensor arrays and the original image. For gray-scale scanning there may be only a single linear array of photosensors. In general, a color scanner measures the intensity of at least three relatively narrow bands of wavelengths of visible light, for example, bands of red, green and blue. A color scanner may sequentially present multiple bands of wavelengths to a single row of sensor elements by sequentially moving color filters into the light path or by sequentially activating different colored light sources. For higher speed, a color scanner may simultaneously present multiple bands of wavelengths to multiple rows of sensor elements.

FIG. 1 illustrates a typical color scanning assembly for an image scanner or copier using filters. For a film scanner, light is provided by a white light source 101 and is transmitted through a transmissive film 100. An optics assembly 102 focuses light from three separate lines on the film 100, through color filters 104, and onto a three-line photosensor array 106. Typically, the light path is folded by mirrors (not illustrated). An entire image is scanned by providing relative movement between the film 100 and the photosensor array 106 (relative movement in the Y-dimension as illustrated by the arrow 108).

FIG. 2 illustrates an alternative color scanning assembly using a beam splitter. Light is provided by a white light source 201 and is transmitted through a transmissive image 200. An optics assembly 202 focuses light from a single line on film 200, through a beam splitter 204 that splits the light into three relatively narrow bands of wavelengths, each band focused onto a different linear array on a three line photosensor array 206. For additional general background, see for example, K. Douglas Gennetten and Michael J. Steinle, "Designing a Scanner with Color Vision," *Hewlett-Packard Journal*, August, 1993, pp 52–58.

For the configuration illustrated in FIG. 1, for any one line on the film 100, intensity of one color is measured, then at a later time intensity of a second color is measured, and then at a later time intensity of a third color is measured. Therefore, in the configuration illustrated in FIG. 1, memory is required to buffer intensity measurements for a line on the scanned image until the final measurements are completed for that line. In the configuration illustrated in FIG. 2, for any one line on the film 200, intensity measurements for all colors are made simultaneously, thereby eliminating the requirement for buffer memory for multiple scans of a single line.

For film scanners, the digitized image may be degraded by the presence of artifacts on the surface of the film being scanned, such as dust and fingerprints, or defects in the surface of the film being scanned, such as scratches. This is particularly a problem on smaller film formats such as 35 mm film, since the image area is small. For most uses, the image must be magnified, which magnifies the surface artifacts and defects as well. An operator must be meticulous in storing and handling film in order to minimize these artifacts and defects. Various methods of cleaning or repairing the surface of the film have been used by photo professionals, but they are time consuming and difficult, and only partially successful.

When film is scanned electronically, it is possible to use image processing algorithms to try to reduce or eliminate artifacts and defects in the scanned digital image. However, in general, it is very difficult to distinguish a dust particle or scratch from the desired image. Typically, a human operator must identify the artifact or defect in the digital image to be corrected. This is a time consuming and costly process. Some fully automatic algorithms have been tried, but most of these tend to blur the entire image.

There is a need for automatically uniquely distinguishing surface artifacts and defects from features defined in the image on the film and for automatically correcting identified artifacts in digitized images.

SUMMARY OF THE INVENTION

Each point on a transmissive image medium (film) is scanned twice. For one scan, conventional direct visible illumination passes through the image on the film and then onto a sensor, producing the image to be corrected. The second scan provides a defect signature (an image of the surface defects), which is then used by image processing software to suitably alter corresponding areas in the first scan. Multiple example embodiments are disclosed for the defect imaging scan, as follows: an embodiment using bright-field infrared illumination, embodiments using dark-field visible white light illumination with a common optical path for intensity measurement, embodiments using dark-field visible white light illumination with different optical paths for intensity measurement, and an embodiment using dark-field infrared illumination with a common optical path for intensity measurement.

The entire image may be sequentially scanned twice in two separate passes, or each line may be scanned twice on a line by line basis, or separate sensors and optics may be used to simultaneously make two separate intensity measurements for each point or line. Preferably, each line is scanned twice on a line-by-line basis with the resulting data interlaced. Interlacing the data reduces memory requirements and reduces or eliminates image misregistration between scans. With interlaced data, defect detection calculations may be done in real time on a line-by-line basis either in the scanner or in a host computer. The defect signature may be obtained by simple pixel-by-pixel processing (comparing pixel values for corresponding interlaced scan lines).

In some example embodiments requiring dark field illumination, two separate optical paths for illumination are used with a common optical path for intensity measurement. Separate optical paths for illumination may be implemented by providing two separate light sources, one of which is used for bright-field scanning and one of which is used for dark-field scanning. Alternatively, a single light source may be mechanically moved between scans. Alternatively, the light path from a single light source may be redirected along different illumination paths for the two scans through the use of mirrors, light pipes, fibre optics or other optics.

In other example embodiments requiring dark-field illumination, a single illumination source is used but intensity measurements are made along two different optical light receiving paths (as opposed to illumination paths), thereby enabling two simultaneous scans for performance. A separate photosensor array may be used for a simultaneous second scan. Alternatively, a mirror, light pipe, fibre optics or other optics may be used to redirect scattered light along a separate path onto a single photosensor assembly.

In example embodiments requiring infrared light, there is one light source for white light and a second light source for infrared light. Each line is scanned twice, once with just white light illumination and a second time adding infrared illumination. The white light illumination does not need to be off during the second scan and can remain on continuously. The infrared illumination must be capable of fast turn-on and turn-off, which may be accomplished, for example, by using infrared Light Emitting Diodes (LEDs).

DETAILED DESCRIPTION OF THE PREFERRED EMBODIMENT OF THE INVENTION

Figure 1:
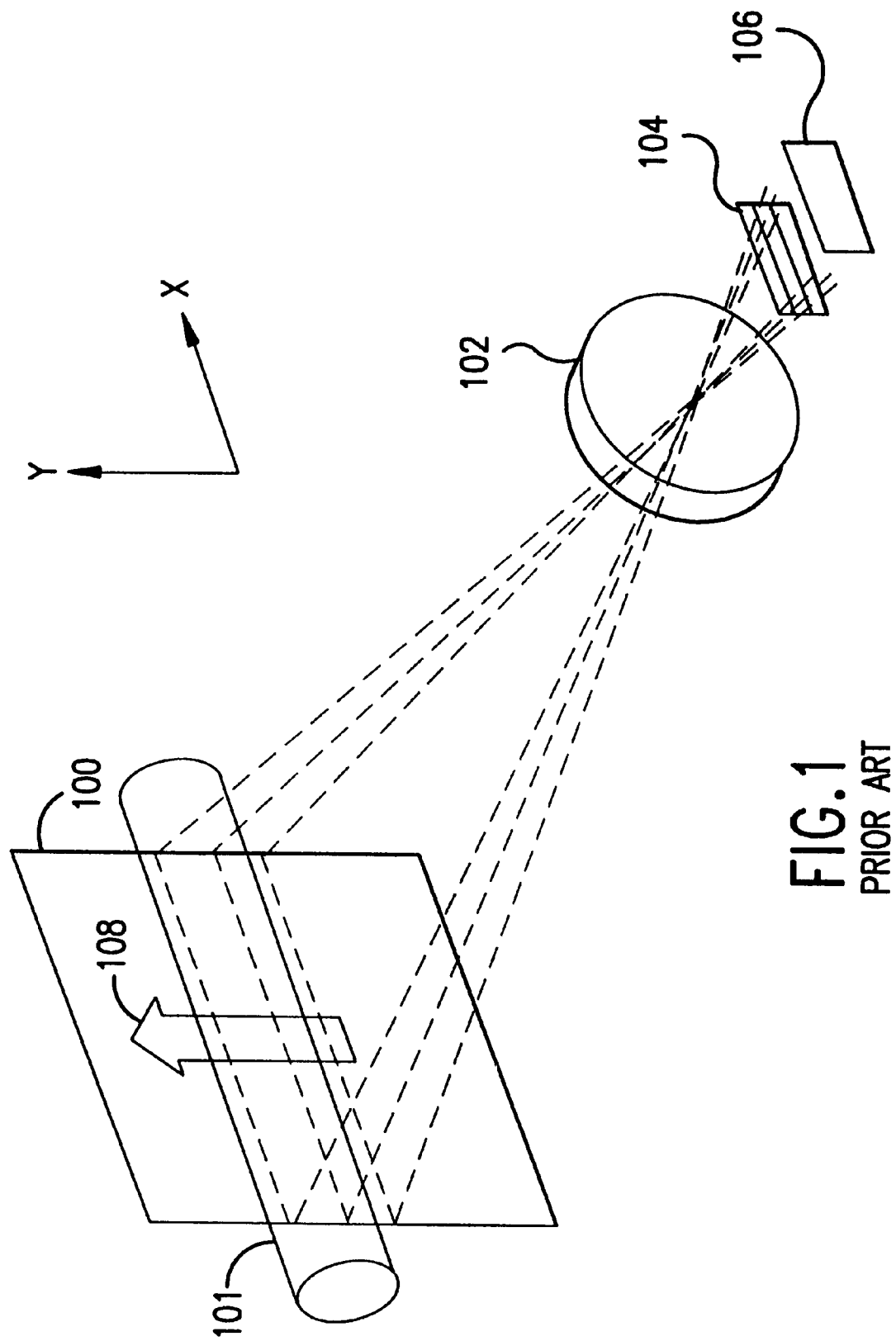
FIG. 1 (prior art) is a block diagram perspective view of a line scanning system with filters.

The following is a brief outline of the detailed description:
1. Overview
2. An embodiment using bright-field infrared illumination
3. Embodiments using dark-field visible white light illumination
   (A) Common optical path for intensity measurement
   (B) Different optical paths for intensity measurement
4. An embodiment using dark-field infrared illumination
5. Characteristics of the data
6. Flow charts of methods

1. OVERVIEW

Figure 5:
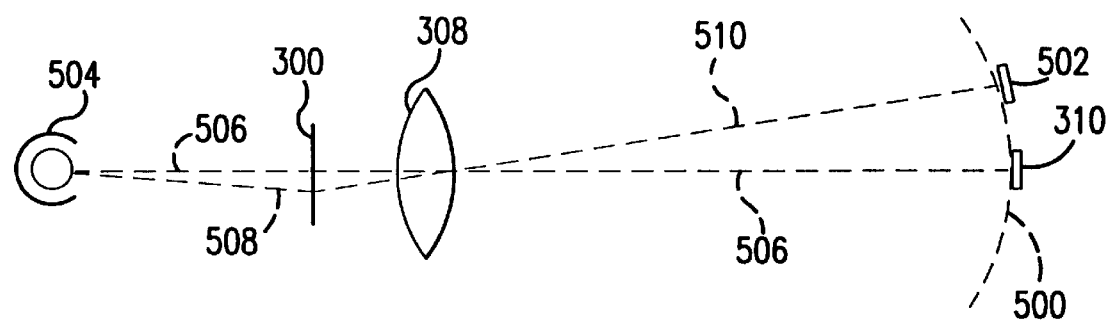
FIG. 5 is a block diagram side view of a scanner in accordance with an alternative example embodiment of the invention with separate or moveable sensor arrays.
Figure 6:
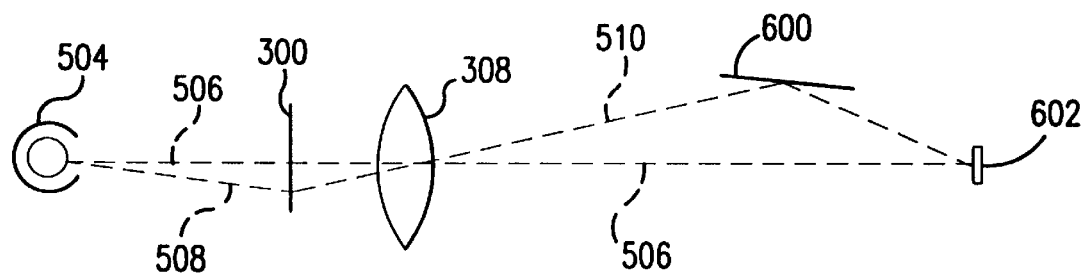
FIG. 6 is a block diagram side view of a scanner in accordance with an alternative example embodiment of the invention with redirection of dark-field light onto a single photosensor assembly.
Figure 7:
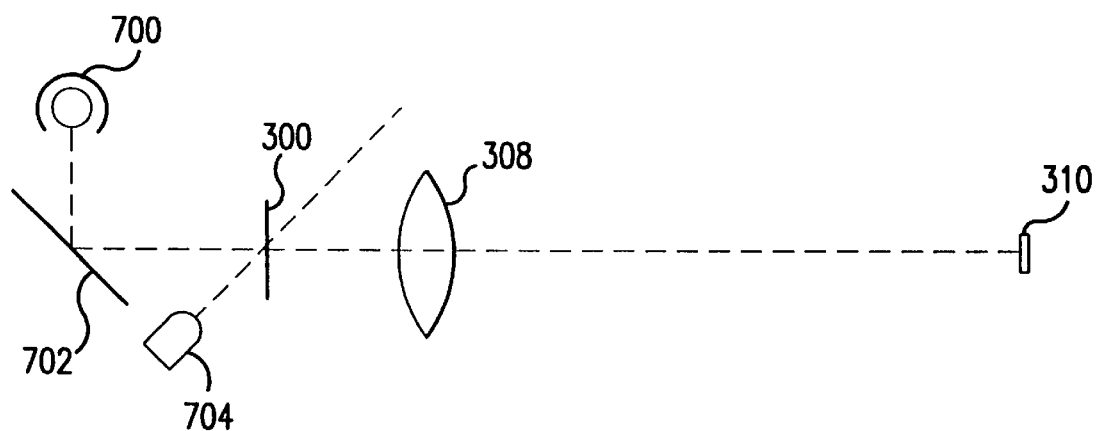
FIG. 7 is a block diagram side view of a scanner in accordance with an alternative example embodiment of the invention employing dark-field infrared light.

There are multiple example embodiments. For color scanning, either color filters as in FIG. 1 or a color separator as in FIG. 2 may be used. In each of the embodiments, two scans, Scan A and Scan B, are performed. Scan A is the normal image scan performed using direct (bright-field) white light, producing the image to be corrected. Scan B provides a defect signature (an image of the surface defects), which is then used by image processing software to suitably alter corresponding areas in the first scan. The order of Scan A and Scan B is not important. Scan B may be performed using bright-field infrared light (FIG. 3), dark-field visible white light (FIGS. 4A, 4B, 4C, 5 and 6) or dark-field infrared light (FIG. 7). Scan B may be performed using separate optical paths for illumination (FIGS. 3, 4A, 4B, 4C and 7), or Scan B may be performed using a separate optical paths for intensity measurement (FIGS. 5 and 6).

On a point-by-point or line-by-line basis, Scan A may be compared to Scan B to identify artifacts. Preferably, to minimize memory requirements, the data stream is interlaced so that for one line on the image, the data for Scan A is followed immediately by the data for the same point or line on the image for Scan B. This eliminates the need for buffering more than one line of data, eliminates image registration problems, and simplifies the processing for speed.

2. BRIGHT-FIELD INFRARED ILLUMINATION

Figure 2:
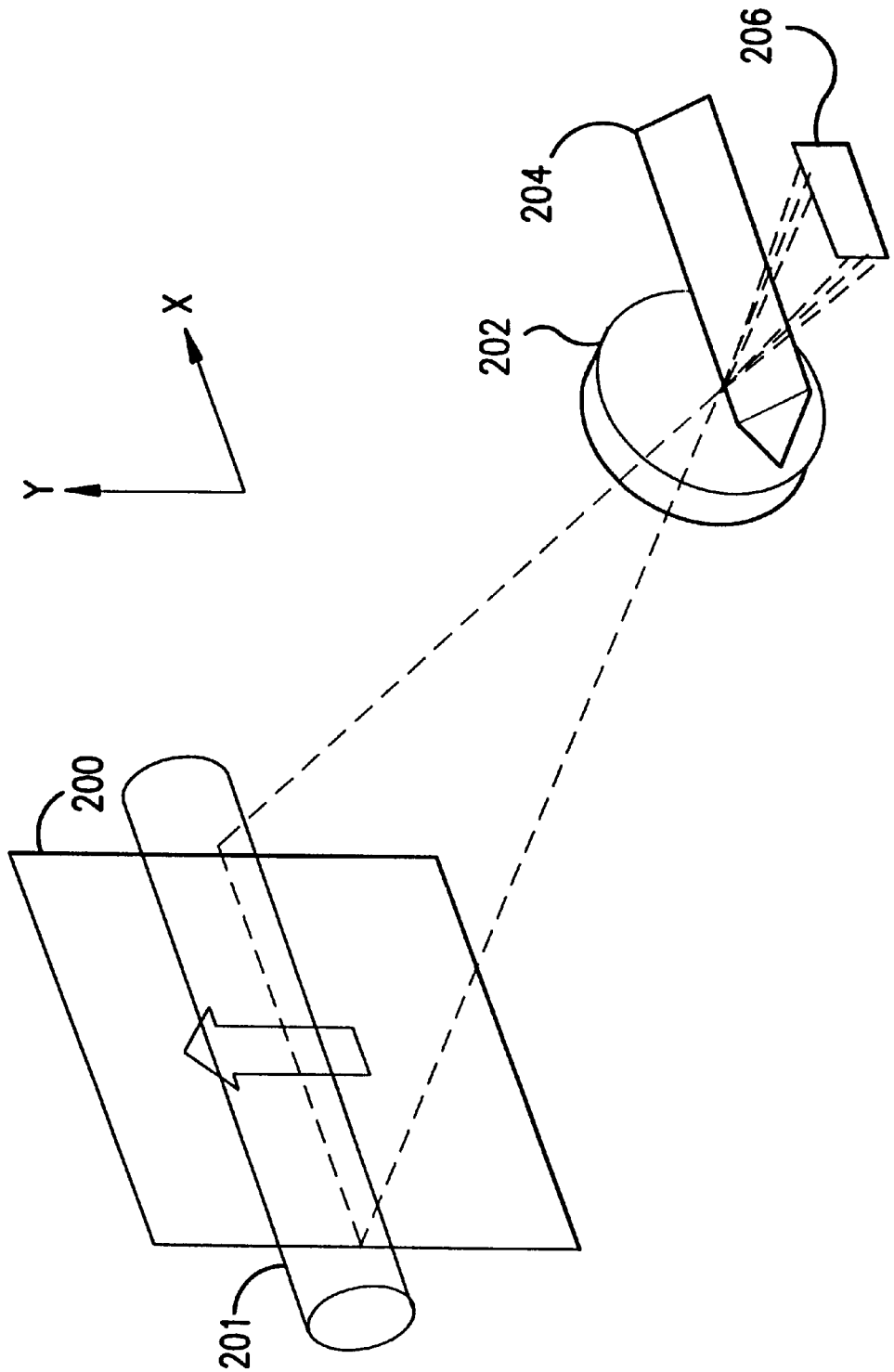
FIG. 2 (prior art) is a block diagram perspective view of a line scanning system with a beam splitter.

In general, the dyes that form an image on processed color photographic film block a narrow band of wavelengths and transmit all other wavelengths. For example, a yellow dye blocks blue wavelengths and transmits all other wavelengths. In general, the film medium and the dyes that form a processed image are transparent to infrared light. In general, in prior art scanners as illustrated in FIGS. 1 and 2, the light source may unavoidably provide some energy at infrared wavelengths. In general, CCD arrays and other photo sensors are sensitive to infrared wavelengths. Typically, in prior art scanners as illustrated in FIGS. 1 and 2, an infrared filter is placed somewhere in the light path to block infrared light (see, for example, U.S. Pat. No. 5,665, 963).

Figure 3:
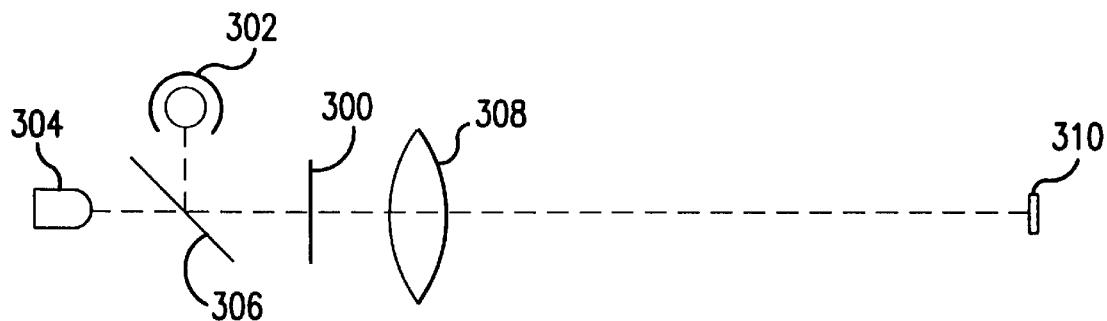
FIG. 3 is a block diagram side view of a film scanner in accordance with an example embodiment of the invention with a white light source and a bright-field infrared source.

FIG. 3 is a simplified illustration of an image scanner for transmissive images in accordance with a first example embodiment of the invention. In FIG. 3, a transmissive image medium (film) 300 is illuminated by a white light source 302 and by an infrared light source 304. A "cold mirror" 306 reflects white light but transmits infrared light. A point or line or area on an image on the surface of the transmissive medium 300 is imaged by an optics system 308 onto a photosensor array 310. The white light source 302 may be, for example, a fluorescent lamp. The infrared light source 304 may be, for example, one or more infrared light emitting diodes (LEDs). Note that the positions of the white light and the infrared light may be reversed by use of a "hot mirror" which reflects infrared light and transmits white light. For either configuration, mirror 306 prevents infrared light from the white light source 302 from reaching the transmissive medium 300.

The entire image could be scanned using white light (302) followed by the entire image being scanned using infrared light (304), or vice versa. However, two separate full-image scans would require the scanner mechanism to have sub-pixel repeatability, or for the software to have very sophisticated (time consuming) algorithms to re-align the two images. In addition, two separate full-image scans would require sufficient memory to hold one additional scan. Therefore, switching between white light and infrared light on a scan-line by scan-line basis is preferred to avoid mechanical positioning inconsistency, sophisticated algorithms, and additional memory. In the configuration illustrated in FIG. 3, infrared LEDs may be rapidly switched on and off. The mirror 306 may be stationary and the white light source may be left on for both scans. Alternatively, mirror 306 may be mechanically moved or rotated so that on a scan-line by scan-line basis the transmissive medium 300 is not exposed to white light during each infrared scan.

For slides, dust and scratches appear as dark areas in the resulting printed images. For negatives, light and dark are reversed for printing so that dust particles or scratches appear as white areas in the resulting printed images. For either slides or negatives, the signal from the photosensors 310 during a white light scan has some varying intensity across the scan line, with occasional low intensity areas (see FIG. 8A, discussed in more detail below). The low intensity areas may be a valid part of the image (for example a whisker on a cat or a power line against the sky in a slide or a reflective highlight in a negative), or the low intensity areas may be caused by an artifact. For slides or negatives, the signal from the photosensors 310 during an infrared scan has a background of high intensity and the background intensity may be made sufficient to saturate the photosensor array. Because the dyes are transparent to infrared, dark areas in the dyes in the image do not show up as low intensity areas in the infrared scan. In the bright-field infrared scan, low intensities at the photosensor occur only where the infrared light is blocked (that is, when an artifact is present)..

For each scan line, image processing is then used on a pixel by pixel basis to remove image areas from the white light scan corresponding to low intensity areas in the infrared scan. Then, image processing software is used to fill the resulting blank areas in the white scan with colors (or patterns or textures) corresponding to the surrounding areas. Filling may be performed on a line by line basis. For example, for each scan line, given a blank area with a left edge and a right edge, the image processing software may interpolate from the color of the pixel just to the left of the left edge of the blank area to the color of the pixel just to the right of the right edge of the blank area. Alternatively, filling may be performed on a two dimensional white light scan with two dimensional blank areas. For example, a nearby "patch" of pixels may be replicated within a blank area to duplicate 2-dimensional patterns or textures. Known image processing techniques such as area size thresholding, feature clustering, edge detection and boundary following, and region extraction methods may be used to limit image correction to larger features and to ignore small scattered points of low intensity and noise in the infrared scan.

For some photosensor technologies, bright-field infrared scanning as in FIG. 3 is a suitable alternative. However, for CCD's, saturation may result in blooming, smearing, and other image degradation problems. Various technologies have been employed in 2-dimension CCD arrays for video cameras to reduce the negative effects of saturation, but in general these technologies add complexity and cost. Therefore, for photosensor arrays employing CCD's, one of the following alternative embodiments employing dark-field illumination may be preferred.

3. DARK-FIELD VISIBLE WHITE LIGHT ILLUMINATION

An alternative method of imaging only the artifacts on the surface of a medium is to use dark-field illumination, in which the light being measured is reflected, scattered, diffracted or otherwise redirected by the artifacts. The general idea of using scattered light to image surface features is known in dark-field imaging in reflection microscopy. However, in dark-field microscopy, the scattered light image is the desired image. For example, the goal might be to image features on the surface of an integrated circuit. In contrast, in the present patent document, the scattered light image is used to identify defective areas to be removed from a corresponding desired image obtained by using direct light.

(A) COMMON OPTICAL PATH FOR INTENSITY MEASUREMENT

Figure 4A:
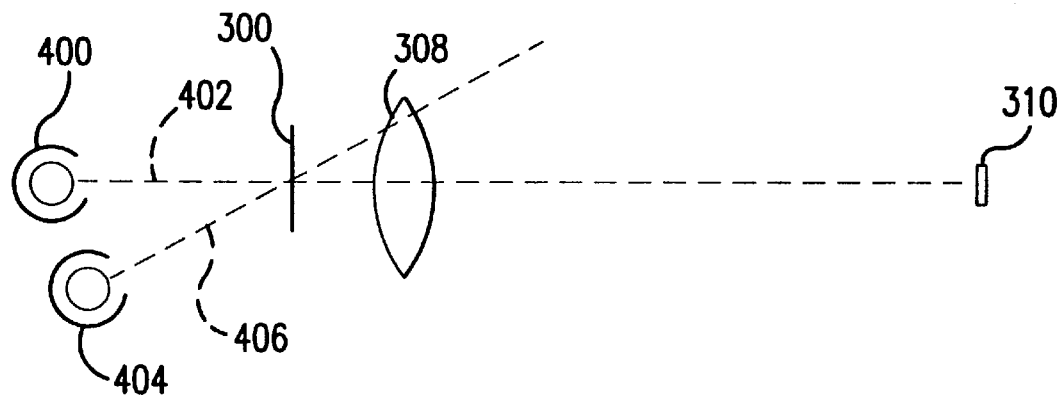
FIG. 4A is a block diagram side view of a film scanner in accordance with an example embodiment of the invention using dark-field illumination with separate or moveable light sources.

FIG. 4A illustrates an example embodiment employing multiple light sources or a moveable light source. In FIG. 4A, a transmissive medium 300 is illuminated by a first light source 400. A light ray from a first white light source 400 passes along a first optical path 402, through a point or line on an image on a transmissive medium or film 300, through an optics system 308, and the point or line on the film 300 is focused onto a photosensor array 310. A second light ray from a second light source 404 passes along a second optical path 406 through the image on the film 300. If there are no artifacts or defects on the surface of the film 300 where optical path 406 passes, then no light from the second light source 404 is projected onto the photosensor array 310. If, however, light along the second optical path 406 hits an artifact or defect, some light may be scattered, reflected, refracted, diffracted or otherwise redirected through the optics system 308 and focused onto the photosensor array 310. The second light source 404 may be a separate light source, or light source 404 may be light source 400 mechanically moved to a different position.

Figure 4B:
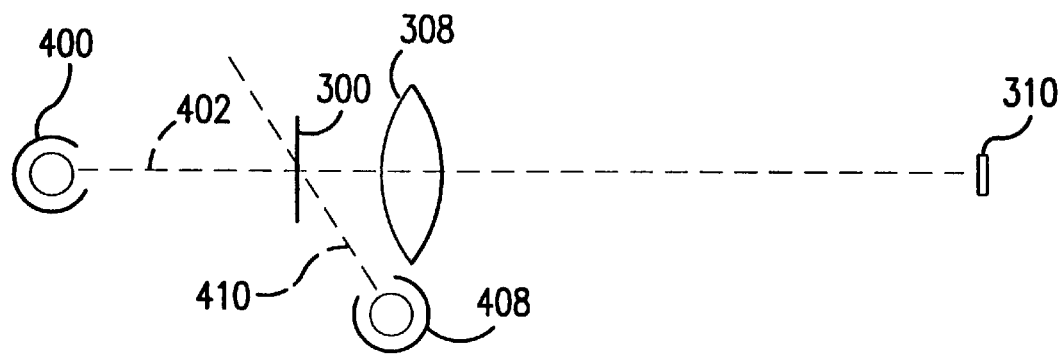
FIG. 4B is a block diagram side view of a film scanner in accordance with an alternative arrangement of the example embodiment of FIG. 4A.

FIG. 4B is a simplified illustration of a variation of the example embodiment of FIG. 4A. In FIG. 4B, a second light source 408 is placed on the opposite side of the film 300 from the first light source 400. Surface defects on either side of the film 300 may scatter, reflect, refract or diffract light from light source 408 through the optics system 308 and onto the photosensor array 310.

Figure 4C:
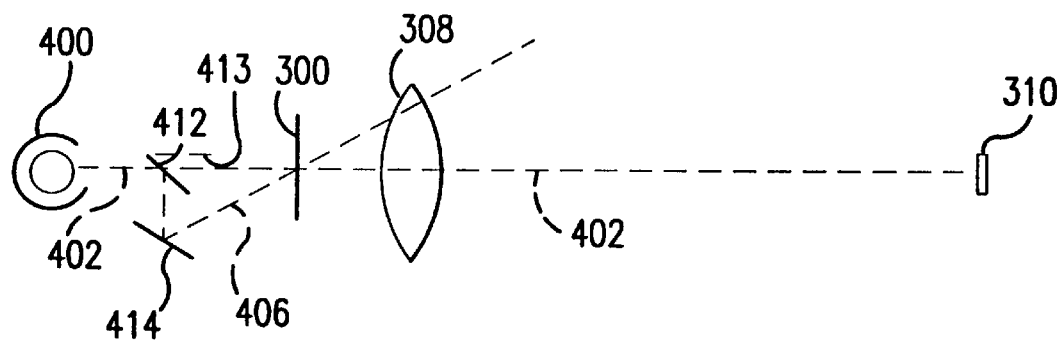
FIG. 4C is a block diagram side view of a film scanner in accordance with an alternative arrangement of the example embodiment of FIG. 4A.

FIG. 4C is a simplified illustration of another variation of the example embodiment of FIG. 4A. In the embodiment of FIG. 4C, instead of two separate light sources or a moveable light source, the illumination light path is altered by the use of mirrors. In FIG. 4C a light ray along optical path 402 is reflected off of mirror 412 and mirror 414 to pass light along optical path 406 through the image on the film 300 along the same direction as optical path 406 in FIG. 4A. Mirror 412 may be moved to the position indicated by reference number 413 to enable a scan with illumination path 402 through the image as in FIGS. 4A and 4B. Light pipes, fiber optics or other optics may be used to deflect the light beam instead of mirrors. The mirrors or other light path redirection devices may be made moveable or rotating to provide alternate illumination paths for switching illumination paths on a scan-line by scan-line basis.

(B) DIFFERENT OPTICAL PATHS FOR INTENSITY MEASUREMENT

In the embodiments of FIGS. 3, 4A, 4B, and 4C, two separate scans are required for each scan line. Scanning speed may be improved by providing two simultaneous scans for each scan line. FIG. 5 illustrates an alternative example embodiment in which two separate photosensor arrays provide two simultaneous scans. In general, an optical system focuses light onto a three dimensional surface, as depicted in two dimensions as a dashed line curve 500 in FIG. 5. In FIG. 5, a second sensor array 502 is positioned along the focal surface 500 of the optics system 308. A light ray from white light source 504 along optical path 506 is focused onto sensor array 310. Typically, scanner light sources are not collimated. Therefore, some light from light source 504 is along an optical path 508 that is different than optical path 506. If there are no artifacts or defects on the surface of the film 300 on optical path 508, no light from the light source 504 impinges onto photosensor array 502. If there are artifacts or defects, a light ray along optical path 508 may be partially scattered, refracted, reflected, diffracted or otherwise redirected onto optical path 510 and focused onto sensor array 502. Note that photosensor array 502 may be a separate photosensor array, or photosensor array 502 may be photosensor array 310 mechanically moved to a different position. However, for speed, photosensor array 502 is preferably separate. Note that photosensor array 502 may be a single line array for a single color or gray. Finally, note that the line on the film 300 being focused onto sensor array 310 is different than the line on the film 300 being focused onto sensor array 502. Alternately worded, the simultaneous scans are performed on different lines on the image. Therefore, memory is required to buffer intensity measurements for a first scan of each line on the scanned image until the second scan is completed for each line, as discussed in conjunction with FIG. 1.

The embodiment of FIG. 5 may require a second photosensor array displaced from a first photosensor array. FIG. 6 illustrates an alternative example embodiment in which a mirror is used to redirect dark-field illumination onto an additional row of a single photosensor assembly. In FIG. 6, a mirror 600 (or fiber optics, light pipe or other optics) redirects a scattered, reflected, refracted or diffracted light ray along optical path 510 back onto a separate sensor row of photosensor array 602. For example, photosensor array 602 may have 3 rows of sensors for red, green, and blue wavelengths for optical path 506 and a separate fourth row for receiving light reflected from mirror 600. Again, as in FIG. 5, there is no light along optical path 510 unless light along path 508 is scattered, reflected, refracted, diffracted or otherwise redirected at the surface of the film 300 onto optical path 510. Again, as in FIGS. 1 and 5, memory is required to buffer intensity measurements for a line on the scanned image until the final measurements are completed for that line.

4. DARK-FIELD INFRARED ILLUMINATION

With white light dark-field imaging as in FIGS. 4A, 4B, 4C, 5 and 6, some of the light scattered or redirected by surface artifacts may be partially blocked by dyes in the image on the film. In particular, with artifacts on relatively dark areas of the image, the scattered light from the artifacts may be substantially reduced by the dyes in the dark areas. The response of the human eye to intensity of light is approximately logarithmic, so that the human eye is very sensitive to small changes in areas of low intensity. Therefore, dark artifacts in dark areas may still be objectionable. Recall, however, that the dyes for color images on film are essentially transparent to infrared light. Therefore, with infrared light, the dyes on the film do not interfere with dark-field imaging. FIG. 7 illustrates an alternative example embodiment of the invention employing infrared dark-field imaging. In FIG. 7, a white light source 700 projects light off of a cold mirror 702 (reflects white light, transmits infrared), through the film 300 and optics system 308 and onto the photosensor array 310. An infrared light source 704 projects light along a path such that no light from the infrared light source 704 reaches the photosensor array 310 unless it is redirected at the surface of the film 300. An artifact at the surface of the film 300 will scatter, reflect, refract, diffract or otherwise redirect the infrared light through the optics system 308 and onto the photosensor array 310. As with the embodiment of FIG. 3, the infrared light source 704 may be rapidly pulsed on and off and the white light source 700 can remain on all the time. Then, with the white light source 700 on continuously, Scan A is performed with the infrared source 704 off and Scan B is performed with the infrared source on.

Scanners typically include a processor and memory. Therefore, image correction processing may be performed within the scanner using a processor within the scanner. Alternatively, both Scan A and Scan B may be uploaded to a host computer for processing within the host computer. For FIG. 7, data for one scan-line using bright-field visible white illumination (Scan A) is preferably interlaced with data for one scan-line using dark-field infrared plus bright-field visible white (Scan B). This reduces memory requirements and reduces the probability of image misregistration between scans. For artifact identification, Scan A may simply be subtracted from Scan B, so that essentially all the bright-field visible white light data cancels everywhere except where there is an artifact. Values in the subtracted data that exceed a threshold are identified as artifacts. In particular, subtraction of interlaced lines as for FIG. 7 may easily be a real time operation performed in a scanner. The embodiment of FIG. 7 then has the following attributes:

1. Processing for artifact detection is simple and fast (a subtraction and a threshold compare).
2. Infrared light enables identification of artifacts in the dark areas of the image.
3. Sensors are not saturated for artifact identification.
4. Memory requirements are minimized.
5. Interleaving alternate scans minimizes potential registration problems.

As a alternative to the embodiment of FIG. 7, a second photosensor array as in FIG. 5 or a mirror for redirection onto an additional row of a photosensor array as in FIG. 6 may be employed to enable simultaneous direct white light and dark-field infrared scanning. That is, one sensor array may image a line of direct white light and a second sensor array may simultaneously image a separate line of dark-field infrared light.

Note that a fluorescent lamp typically cannot be rapidly switched on and off. In addition, when a fluorescent lamp is first turned on, typically a substantial amount of time (greater than 5 seconds) is required for the light intensity to stabilize. Therefore, for the embodiment of FIGS. 3 and 7, it is preferable to be able to leave the fluorescent lamp on continuously and pulse infrared LEDs. Many other variations are possible. For example, for the embodiments of FIGS. 3 and 7, instead of separate light sources, one light source with both white and infrared light could be used, and hot mirrors, cold mirrors or filters could be inserted and removed from the light path for Scan A and Scan B. Alternatively, LED's could be used for the white light source (for example, red, green and blue LED's) along with infrared LED's, and both the white and the infrared light sources could then be rapidly pulsed on and off.

5. CHARACTERISTICS OF THE DATA

FIGS. 8A–8E illustrate graphs of intensity versus pixel number for a portion of a scan line on an image as measured by a photosensor line array (one color or gray scale) for some of the embodiments discussed above. In a photosensor array using a different line of photosensors for each color (for example, red, green blue), defect measurement may be performed using only one color (for example, green). FIGS. 8A–8E may be viewed as representing data for scans of slides where a large measured intensity value represents light areas in the original image and a small intensity value represents dark areas in the original image. Note however that for scans of negative film strips, the relationship between measured intensity and lightness in the original image is reversed. In addition, depending on sensor implementation, small numbers may represent high intensity and large numbers may represent low intensity. Therefore, depending on implementation, the graphs may need to be vertically reversed.

Figure 8A:
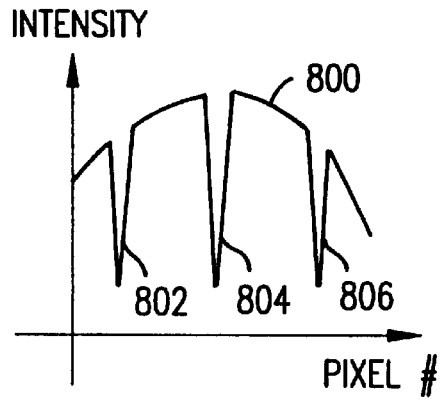
FIGS. 8A–8E are graphs illustrating intensity profiles for a portion of a scan line on an image as measured using various example embodiments of the invention.

FIG. 8A illustrates a direct (bright-field) white light scan, which is called Scan A in the various embodiments. The intensity profile 800 has three areas 802, 804 and 806 where the intensity drops to low levels. These low levels may be caused by defects or by a valid dark line in the image.

Figure 8B:
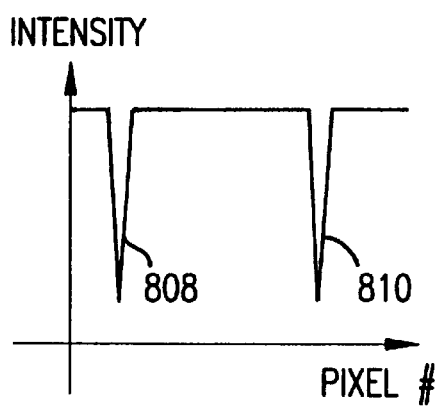

FIG. 8B illustrates an intensity profile for the image of FIG. 8A as measured using direct infrared illumination only, for example the embodiment of FIG. 3 with the white light off. With sufficient infrared illumination intensity, the photosensor array may be saturated everywhere except at areas 808 and 810. Areas 808 and 810 represent areas that are opaque to infrared light, and are therefore artifacts. Comparing FIGS. 8B and 8A, areas 802 and 806 of FIG. 8A must be artifacts as identified in FIG. 8B, and area 804 of FIG. 8A must be a legitimate part of the image because it is essentially transparent to infrared light as illustrated in FIG. 8B.

Figure 8C:
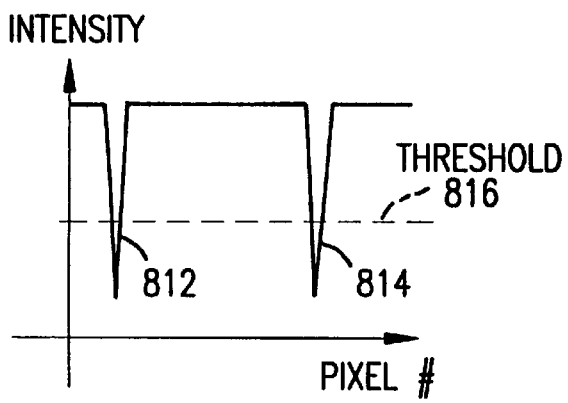

FIG. 8C illustrates an intensity profile for the image of FIG. 8A as measured using both direct infrared illumination and white light, for example the embodiment of FIG. 3 with both light sources on. With infrared illumination sufficient to saturate the photosensor array for all areas except for artifact areas 812 and 814, FIG. 8C is essentially identical to FIG. 8B. Therefore, with a suitable threshold 816, any areas having an intensity below the threshold 816, such as areas 812 and 814, must be artifacts that need correcting. FIG. 8C illustrates that the white light in FIG. 3 may be left on and artifacts can still be identified.

Figure 8D:
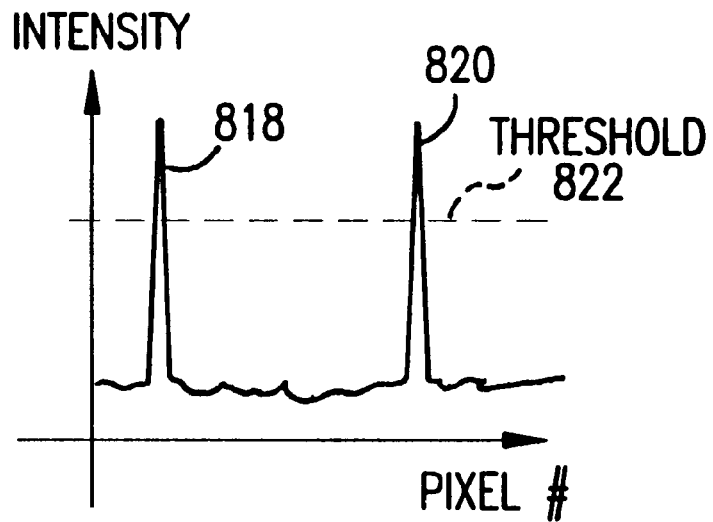

FIG. 8D illustrates the image of FIG. 8A illuminated by dark-field infrared only, for example as in FIG. 7 with the white light off, or with an infrared light as in FIG. 7 with a separate sensor array as in FIGS. 5 and 6. In FIG. 8D, there is a general low background intensity with two higher intensity areas 818 and 820. Note that FIG. 8D may also represent a scan with dark-field white light only, but the amplitude of areas 818 and 820 may be reduced by dyes in the image for dark-field white light.

Figure 8E:
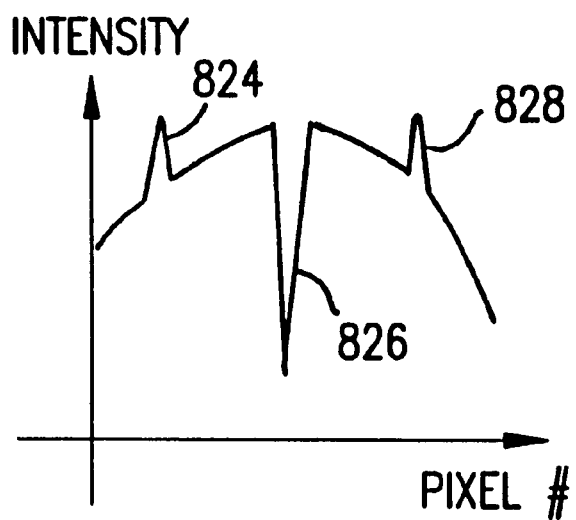

FIG. 8E illustrates the image of FIG. 8A illuminated by both bright-field white light and dark-field infrared light, for example, as in FIG. 7 with both light sources on. Depending on the intensity of the infrared light source, the dark-field infrared illumination may cause areas 824 and 828 (corresponding to FIG. 8A, areas 802 and 806, respectively, and FIG. 8D, areas 818 and 820, respectively), to be more intense than the image, as illustrated, or areas 824 and 828 may be less intense. However, in general, adding dark-field infrared illumination to the measurement of FIG. 8A will change the intensity of artifact areas (802, 806) and will have little impact on low intensity areas caused by legitimate dark areas in the image. If the data of FIG. 8A is subtracted from the data of FIG. 8E, the data resulting from the legitimate image will cancel, and the result will be as illustrated in FIG. 8D. That is, white plus dark-field infrared intensity data minus white intensity data approximately equals dark-field infrared intensity data. By comparing the subtracted data to a threshold as in threshold 822 in FIG. 8D, artifacts may be identified. By establishing a threshold 822, a processor can determine that areas 802 and 806 in FIG. 8A, corresponding to areas 818 and 820 in the subtracted data (FIG. 8D), are artifacts to be corrected. As with FIG. 8C, FIG. 8E illustrates that artifact detection may be made without having to turn the white light source off. Therefore, the embodiments of FIGS. 3 and 7 provide suitable results with substantial simplicity of design. Recall, however, for the embodiment of FIG. 3, saturating photosensor elements as depicted in FIGS. 8B and 8C may be undesirable.

6. FLOW CHARTS OF METHODS

Figure 9:
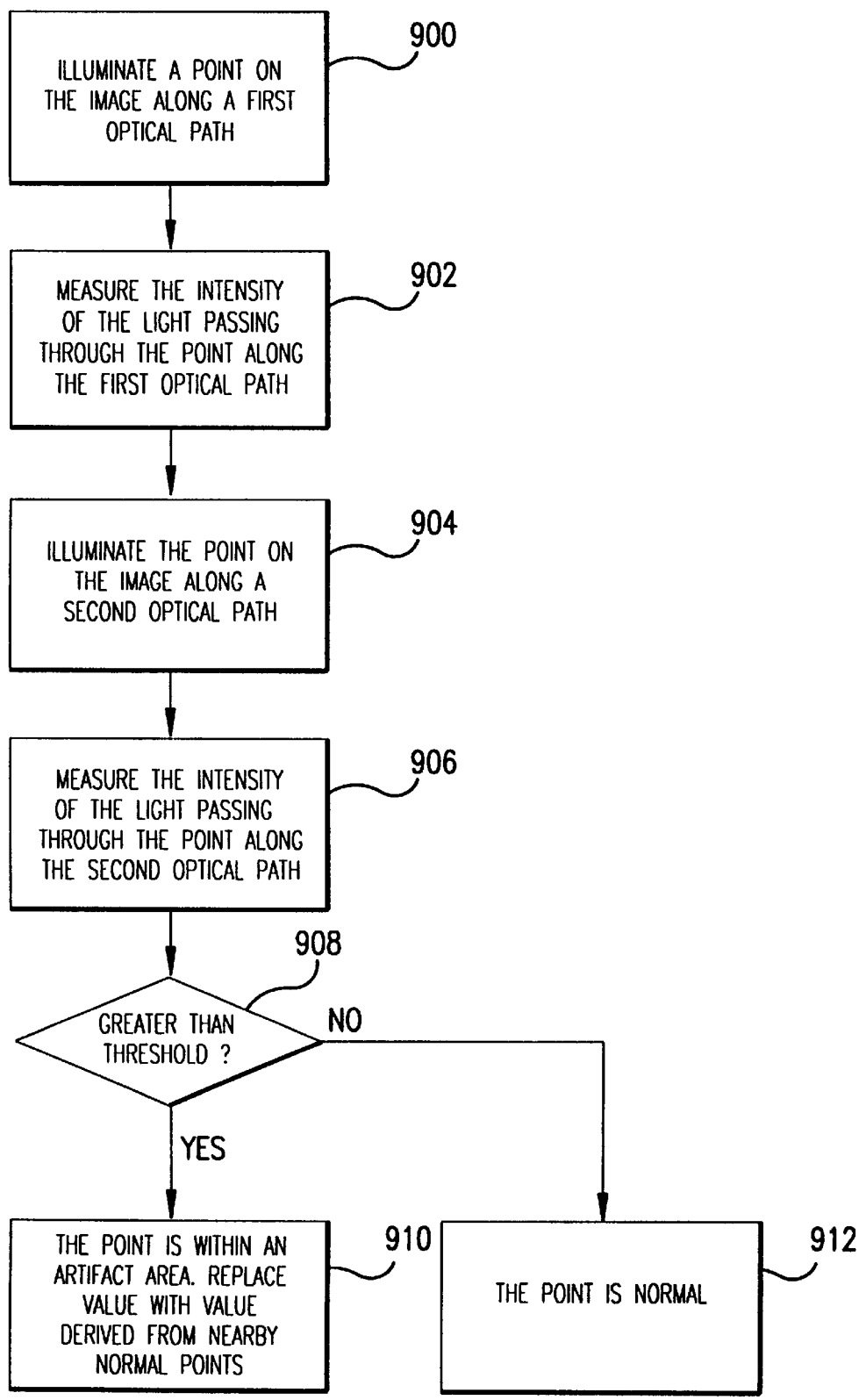
FIG. 9 is a flow chart of a method of detecting and correcting surface artifacts using separate optical paths for illumination.

FIG. 9 is a flow chart of a method of detecting surface artifacts in accordance with the embodiments of FIGS. 3, 4A–4C, 5 and 6. First, at steps 900 and 902, a point on the film is illuminated along a first optical path and the intensity is measured. Next (steps 904 and 906), the intensity of the light passing through the point along a second optical path is measured. Note that the second optical path may be obtained by using separate illumination paths (FIGS. 3, 4A, 4B, 4C) or by using separate detection paths (FIGS. 5 and 6). Note also that the second scan (steps 904, 906) may be with white light plus direct (bright-field) infrared light (FIG. 3) or dark-field white light (FIGS. 4A, 4B, 4C, 5, 6). If the intensity measured in step 906 exceeds a predetermined threshold (test 908), the point is identified as an artifact (step 910). Note that decision 908 specifies that an artifact intensity is greater than a threshold. However, the sense of the measurement relative to a threshold may vary, for example, exceeding a threshold in FIG. 8B designates an artifact whereas falling below a threshold in FIG. 8E indicates an artifact. If the point is identified as an artifact, the measured intensity for the point during the bright-field white light scan is replaced (step 912) with a measurement derived from neighboring normal points, using methods described earlier. Otherwise, the point is normal (step 914).

Figure 10:
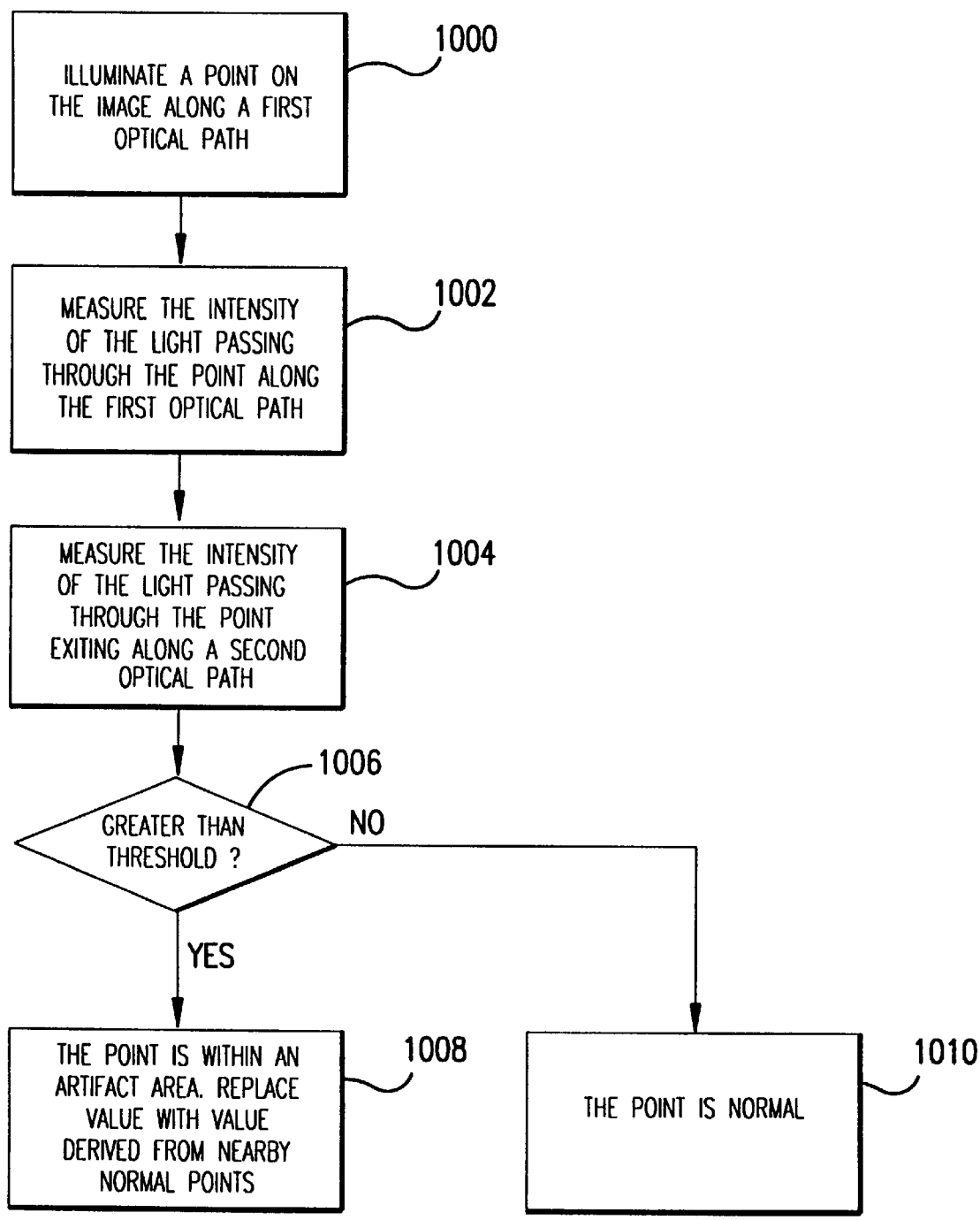
FIG. 10 is a flow chart of a method of detecting and correcting surface artifacts using separate optical paths for intensity measurements.

FIG. 10 is a flow chart of a method of detecting surface artifacts consistent with FIGS. 5 and 6. First, at steps 1000 and 1002, a point on the film is illuminated along a first optical path and the intensity is measured. Next (step 1004), at a later time, the intensity of the light passing through the point along a second optical path is measured. Note that there are two simultaneous scans for performance, but for any measured point on the image, measurements 1002 and 1004 are made at different times. If the intensity measured in step 1004 exceeds a predetermined threshold (test 1006), the point is identified as an artifact (step 1008). Again, in some embodiments falling below a threshold may indicate an artifact. Otherwise, the point is normal (step 1010). If the point is identified as an artifact, the measured intensity for the point in the first scan is replaced (step 1012) with a measurement derived from surrounding normal points, using methods described earlier.

Figure 11:
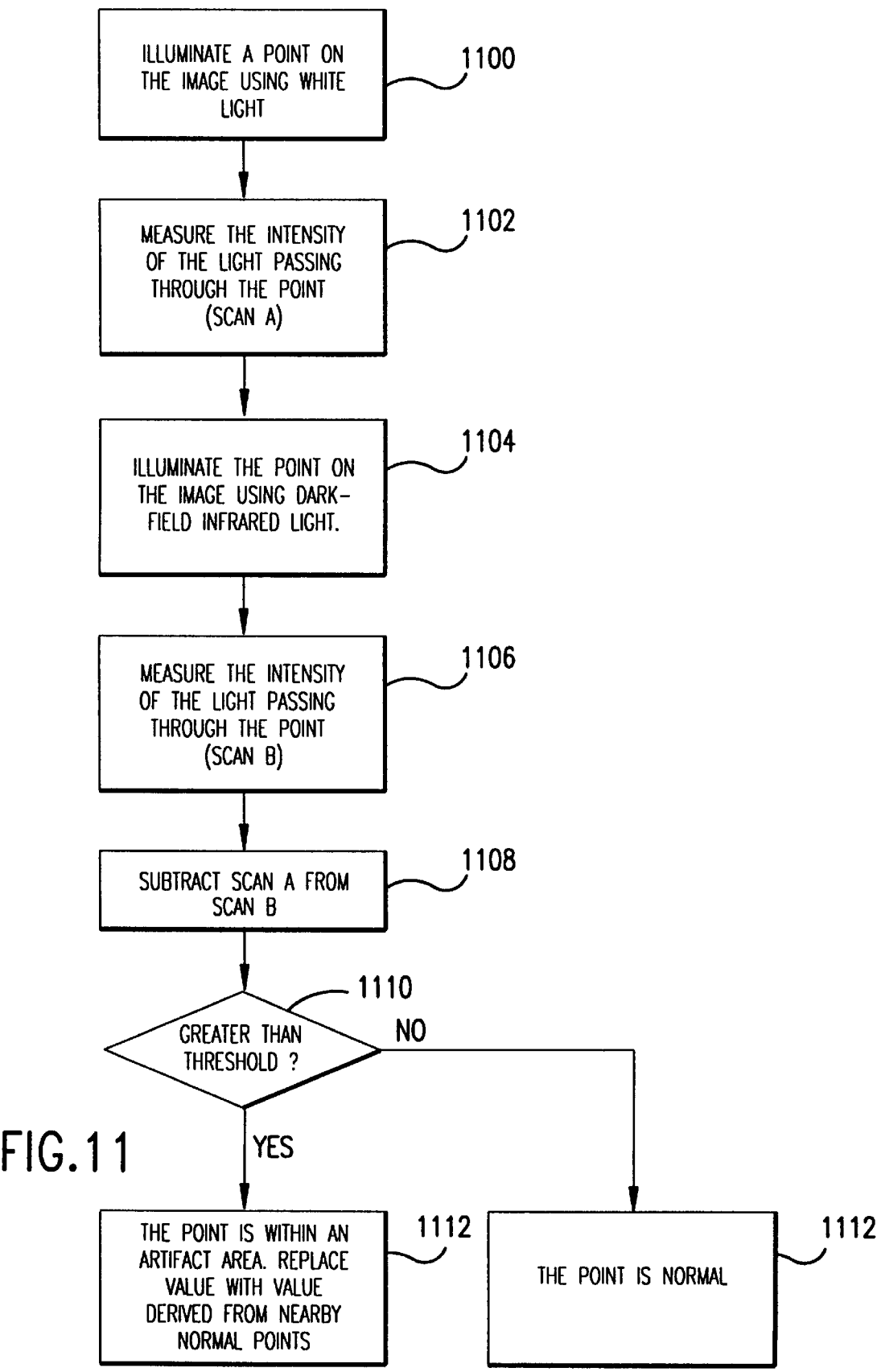
FIG. 11 is a flow chart of a method of detecting and correcting surface artifacts using dark-field infrared illumination.

FIG. 11 is a flow chart of a method of detecting surface artifacts consistent with FIG. 7. First, at steps 1100 and 1102, a measurement is made with white light only (Scan A). Then, at steps 1104 and 1106, a measurement is made with white light plus dark-field infrared (Scan B). Then, Scan A is subtracted from Scan B (step 1108). If the value at a point after subtraction exceeds a predetermined threshold (test 1110), the point is an artifact and its value is replaced by a value derived from neighboring points (step 1112). Otherwise the point is normal (step 1114).

The example embodiments have been illustrated using line-by-line scanning. However, the general method of using scattered or diffracted light to detect artifacts is equally applicable to scanners that sequentially measure intensity one point at a time or for digital cameras having two dimensional photosensor arrays that detect intensity at all points simultaneously.

The foregoing description of the present invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of detecting surface artifacts on a transmissive image medium, the method comprising the following steps:
   (a) providing illumination through the medium, at a point, along a first optical path;
   (b) measuring light intensity along a second optical path that passes through the point on the medium, the second optical path being different than the first optical path, so that the measured light intensity results from light along the first optical path being redirected onto the second optical path at the point on the medium;
   (c) comparing the intensity measured in step (b) to a predetermined threshold; and
   (d) identifying the point on the medium as a surface artifact on the medium as a result of the comparison of step (c).

2. The method of claim 1, further comprising:
   replacing an intensity measurement for the point on the medium, when the point on the medium is identified as a surface artifact on the medium, with a value derived from intensity measurements of nearby points that are not identified as surface artifacts on the medium.

3. The method of claim 1 wherein the illumination provided in step (a) includes infrared wavelengths.

4. The method of claim 1 wherein step (d) further comprises identifying the point on the medium as a surface artifact if the intensity measurement of step (b) exceeds the predetermined threshold.

5. The method of claim 1 wherein step (d) further comprises identifying the point on the medium as a surface artifact if the intensity measurement of step (b) is below the predetermined threshold.

6. A method of detecting surface artifacts on a transmissive image medium, the method comprising the following steps:
   (a) providing illumination through the medium, at a point, along a first optical path;
   (b) measuring light intensity that passes through the point along the first optical path;
   (c) measuring light intensity along a second optical path that passes through the point on the medium, the second optical path being different than the first optical path, so that the measured light intensity results from light along the first optical path being redirected onto the second optical path at the point on the medium;
   (d) computing a difference between the measurement of step (b) and the measurement of step (c);
   (e) comparing the result of step (d) to a predetermined threshold; and
   (f) identifying the point on the medium as a surface artifact on the medium as a result of the comparison of step (c).

7. The method of claim 6, further comprising:
   replacing an intensity measurement for the point on the medium, when the point on the medium is identified as a surface artifact on the medium, with a value derived from intensity measurements of nearby points that are not identified as surface artifacts on the medium.

8. The method of claim 6 wherein step (f) further comprises identifying the point on the medium as a surface artifact if the result of the computation of step (d) exceeds the predetermined threshold.

9. The method of claim 6 wherein step (f) further comprises identifying the point on the medium as a surface artifact if the result of the computation of step (d) is below the predetermined threshold.

10. The method of claim 6, wherein the data of step (b) and the data of step (c) are adjacent within a stream of data.

11. An image scanner comprising:
    a photosensor, the photosensor adapted to receive light along a first light path through a point;
    a light source, the light source adapted to provide light along a second light path through the point, the second light path not directed onto the photosensor; and
    wherein when some of the light from the light source is redirected at the point onto the first light path and onto the photosensor, an artifact is identified at the point.

12. An image scanner comprising:
    a photosensor, the photosensor adapted to receive light through a point along a first light path;
    a first source of light adapted to provide light through the point and along the first light path onto the photosensor;
    a second source of light adapted to provide light through the point and along a second light path, the second light path not directed onto the photosensor; and
    wherein when some of the light from the second source of light is redirected at the point onto the first light path and onto the photosensor, an artifact is identified at the point.

13. The image scanner of claim 12, wherein the first source of light and the second source of light are from separate light sources.

14. The image scanner of claim 12, wherein the first source of light is from a light source providing white wavelengths and the second source of light is from a light source providing infrared wavelengths.

15. The image scanner of claim 12, wherein the first source of light and the second source of light are from one light source.

16. An image scanner comprising:
    a first photosensor, the first photosensor adapted to receive light through a first point along a first light path;
    a second photosensor, the second photosensor adapted to receive light through a second point along a second light path;
    a light source, the light source adapted to provide light through the first point along the first light path and adapted to provide light through the second point that is not along the second light path; and wherein when some of the light from the light source is redirected at the second point onto the second light path and onto the second photosensor, an artifact is identified at the second point.

* * * * *